(12) United States Patent
Van Dinther

(10) Patent No.: US 11,282,364 B2
(45) Date of Patent: Mar. 22, 2022

(54) WRIST-WORN MEDICAL ALERT DEVICE FOR CONVEYING AN EMERGENCY MESSAGE TO A CAREGIVER

(71) Applicant: KONINKLIJKE PHILIPS N.V., Eindhoven (NL)

(72) Inventor: Cornelus Hendricus Bertus Arnoldus Van Dinther, Mierlo (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/054,545

(22) PCT Filed: May 14, 2019

(86) PCT No.: PCT/EP2019/062313
§ 371 (c)(1),
(2) Date: Nov. 11, 2020

(87) PCT Pub. No.: WO2019/219663
PCT Pub. Date: Nov. 21, 2019

(65) Prior Publication Data
US 2021/0248893 A1 Aug. 12, 2021

(30) Foreign Application Priority Data
May 15, 2018 (EP) .................................. 18172328

(51) Int. Cl.
*G08B 21/04* (2006.01)
*A61B 5/00* (2006.01)
(Continued)

(52) U.S. Cl.
CPC ........ *G08B 21/0453* (2013.01); *A61B 5/0022* (2013.01); *A61B 5/1125* (2013.01);
(Continued)

(58) Field of Classification Search
CPC .... G08B 1/00; G08B 21/0446; G08B 25/016; A61B 1/00; A61B 5/0002; A61B 5/0031
See application file for complete search history.

(56) References Cited

U.S. PATENT DOCUMENTS 10,466,783 B2 * 11/2019 Newberry ............... G06F 3/017
2009/0174578 A1 7/2009 Taki
(Continued)

FOREIGN PATENT DOCUMENTS

| EP | 2875778 A1 | 5/2015 |
|---|---|---|
| WO | 2013071014 A2 | 5/2013 |
| WO | 2015121100 A1 | 8/2015 |

OTHER PUBLICATIONS

International Search Report and Written Opinion, International Application No. PCT/EP2019/062313, dated Aug. 20, 2019.

*Primary Examiner* — Hoi C Lau

(57) ABSTRACT

The present invention relates to the field of medical emergency signaling and user-activated medical alarm systems. In particular, a wrist-worn medical alert device (10) for conveying an emergency message to a caregiver (80) is presented, wherein the medical alert device is adapted to be worn at a wrist (101) of a subject (100), the device comprising: a PPG unit (20) adapted to acquire a first PPG signal (26) at first wavelength ($\lambda 1$) and a second PPG signal (25) at second wavelength ($\lambda 2$) over time at the wrist of the subject; a processing unit (30) adapted to receive the first and second PPG signals (25, 26) and to determine a finger movement of one or more fingers (102) of the subject (100) based on the first and second PPG signals; and a communication unit (40) adapted to transmit, based on the determined finger movement, an emergency message to the caregiver (80). The present invention further relates to a corresponding system (1), method (60) and computer program for carrying out said method.

15 Claims, 3 Drawing Sheets

(51) Int. Cl.
  *A61B 5/11*    (2006.01)
  *G08B 25/01*   (2006.01)

(52) U.S. Cl.
  CPC ............ *A61B 5/681* (2013.01); *A61B 5/6824* (2013.01); *G08B 21/0446* (2013.01); *G08B 25/016* (2013.01)

(56) References Cited

U.S. PATENT DOCUMENTS

| | | | |
|---|---|---|---|
| 2014/0221848 A1* | 8/2014 | Nagasaka | A61B 5/02438 |
| | | | 600/479 |
| 2017/0311825 A1* | 11/2017 | Weekly | A61B 5/7207 |
| 2017/0372592 A1* | 12/2017 | Neravati | G08B 27/008 |
| 2019/0286233 A1* | 9/2019 | Newberry | G06F 1/1694 |
| 2020/0004336 A1* | 1/2020 | Newberry | A61B 5/1126 |
| 2021/0169417 A1* | 6/2021 | Burton | A61B 5/02055 |
| 2021/0236011 A1* | 8/2021 | Tarassenko | A61B 5/02416 |
| 2021/0248893 A1* | 8/2021 | Van Dinther | A61B 5/6824 |

* cited by examiner

WRIST-WORN MEDICAL ALERT DEVICE FOR CONVEYING AN EMERGENCY MESSAGE TO A CAREGIVER

CROSS-REFERENCE TO PRIOR APPLICATIONS

This application is the U.S. National Phase application under 35 U.S.C. § 371 of International Application No. PCT/EP2019/062313, filed on 14 May 2019, which claims the benefit of European Patent Application No. 18172328.9, filed on 15 May 2018. These applications are hereby incorporated by reference herein.

FIELD OF THE INVENTION

The present invention relates to the field of medical emergency signaling and user-activated medical alarm systems. In particular, the present invention relates to a wrist-worn medical alert device for conveying an emergency message to a caregiver. The present invention furthermore relates to a corresponding system and method as well as to a corresponding computer program for carrying out said method.

BACKGROUND OF THE INVENTION

Elderly and dependent people are at increased risk regarding medical emergencies and accidents at home. Medical emergencies may arise e.g. when a stroke or heart attack occurs, caused by home accidents, when moving and handling objects, or due slips and falls. In such situations, medical care may be critical. The time elapse from the moment the medical emergency happens to the moment assistance is provided should be minimal, as it may become vital for the individual.

A medical home alarm can refer to an alarm system designed to signal the presence of a hazard requiring urgent attention and to summon assistance such as emergency medical personnel, family members or neighbors. Typical systems have a wireless pendant or transmitter that can be activated by the user in case of emergency. When the medical alarm is activated, the signal can be transmitted to an alarm monitoring company's central station, other emergency agency or other programmed contact. Medical personnel or other assistance can then be dispatched to the site where the alarm was activated. There are different technologies which are able to alert medical assistance.

Firstly, there are so-called health buttons or emergency buttons, wherein a user may manually set off a call for help by pressing an alert button on his personal device. Medical alarm devices may be implemented in different forms such as, for example, a pendant worn around the neck, a small device worn on the belt, or a wristband. Moreover, a user may simply use his smartphone to call for assistance.

However, depending on the severity of the patient's condition, the patient may not be able to properly operate the medical alarm device. For example, the patient may not be able to reach over to activate a wrist-worn alarm button with the other hand.

Automatic monitoring systems, such as fall detection systems, have proven very helpful in such situations.

Further, there are passive systems, similar to a dead-man's switch, which may trigger an alarm if no activity has been detected for a predetermined period of time. However, a drawback of this solution is that a significant amount of time may elapse until assistance can be provided. However, in particular for stroke patients, the time elapsed from the moment the medical emergency happens to the moment assistance is provided is crucial.

In the different application scenario of patient monitoring in hospitals, automatic monitoring systems are widely used. An alarm may e.g. be triggered if a vital sign parameter such as a blood oxygen saturation value falls below a predetermined threshold. However, when using such monitoring systems outside of the well-controlled environment of and intensive care unit (ICU) or hospital, there is a risk of triggering a large number of false alarms. As a solution, WO 2013/071014, paragraph [0012], discloses a body worn patient monitor comprising an alarm system that takes a patient's motion into consideration when processing vital sign measurements. Since motion typically disrupts the RED/IR PPG waveforms for blood oxygen saturation (SpO2) measurement, it is suggested to exclude certain noise-corrupted artifacts from the SpO2 calculations. Hence, the risk of false alarms can be reduced. Moreover, the motion sensor can be used as a fall detector regardless of the SpO2 values of the patient.

However, such systems may only cover a limited number of emergency situations. An alarm may not be triggered when it is needed the most.

SUMMARY OF THE INVENTION

It is an object of the present invention to provide an improved medical alert device. In particular, it would be desirable to provide a medical alert device that can be more easily operated by a user. In particular, it would be desirable to facilitate the dispatch of an alert message in a wider range of emergency situations.

In a first aspect of the present disclosure a wrist-worn medical alert device for conveying an emergency message to a caregiver is presented, wherein the medical alert device is adapted to be worn at a wrist of a subject, the device comprising:
 a PPG (photoplethysmography) unit adapted to acquire a first PPG signal at first wavelength ($\lambda 1$) and a second PPG signal at second wavelength ($\lambda 2$) over time at the wrist of the subject;
 a processing unit adapted to receive the first and second PPG signals and to determine a finger movement of one or more fingers of the subject based on the first and second PPG signals; and
 a communication unit adapted to transmit, based on the determined finger movement, an emergency message to (a communication apparatus of) the caregiver.

In a further aspect of the present disclosure a medical alert system for conveying an emergency message to a caregiver is presented, the system comprising the aforementioned wrist-worn medical alert device; and a base station configured to forward an emergency message from the wrist-worn medical alert device to a caregiver.

In another aspect of the present disclosure, a medical alert method for conveying an emergency message to a caregiver is presented, the method comprising the steps of:
 receiving first and second PPG signals, said first PPG signal being acquired at a first wavelength ($\lambda 1$) and said second PPG signal being acquired at a second wavelength ($\lambda 2$) over time at a wrist of a subject;
 determining a finger movement of one or more fingers of the subject based on the first and second PPG signals; and transmitting, based on the determined finger movement, an emergency message to (a communication apparatus) of the caregiver.

In yet further aspects of the present invention, there is provided a corresponding a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed. It shall be understood that receiving first and second PPG signals in this context can refer to receiving data indicative of first and second PPG signals acquired at a wrist of the subject. Correspondingly, transmitting an emergency message to the caregiver can refer to dispatching or sending data indicative of an emergency message to the caregiver. Reference can be made to a computer-based signal processing method.

Preferred embodiments of the invention are defined in the dependent claims. It shall be understood that the claimed method, system, computer program and medium can have similar and/or identical preferred embodiments as the claimed system, in particular as defined in the dependent claims and as disclosed herein.

Photoplethysmography (PPG) is a known technique for determining vital sign parameters such as the heart rate or blood oxygen saturation of a subject. In intensive care units (ICUs), it is known to automatically issue an alarm if a vital sign parameter does not fall within a predetermined healthy range. For example, an alert may be issued if the blood oxygen saturation drops below a predetermined threshold.

The present invention is based on the idea that a medical emergency condition is not necessarily immediately reflected by a vital sign parameter. Hence, a vital sign-based alert system may only cover a limited number of emergency situations. Nonetheless, wrist-worn devices for vital signs monitoring are becoming increasingly popular for continuous monitoring of vital signs for fitness, leisure and health applications. Motion is usually considered an artifact in PPG measurements. For example, a movement of fingers may substantially distort acquired PPG signals. Therefore, it is usually an object to suppress any motion and corresponding signal portions are usually disregarded to minimize the occurrence of false alarms based on SpO2 measurements.

On the other hand, a convention health button or emergency button does not rely on vital signs measurements. However, such a health button requires that the user is still in a position to reach and activate the health button in order to set off an alarm.

The inventor recognized that a wrist-worn medical alert can be provided wherein an emergency message is generated based on a finger movement of one or more fingers that is determined from PPG measurements at a first and at a second wavelength. The first wavelength and the second wavelength can be different, for example, red and green or red and infrared can be used. Hence, instead of considering a motion signal as an artifact and disregarding the respective signal portions, it is suggested to actually use said finger movement to trigger a user-activated medical alert.

During an emergency some body parts might have become immobilized, such as one or both upper limbs, and operating a conventional patient alert device may be impossible. A conventional health button or emergency button does not rely on vital signs measurements. However, such a health button requires that the user is still in a position to reach the health button in order to set off an alarm and does not have problems operating the device e.g. due to dizziness. The proposed solution overcomes such drawbacks since moving the fingers requires minimal effort and can be done in any body position and without being consciously aware of the device itself.

Often, a wrist-worn device for continuous monitoring of vital signs may be available anyway. An advantage of the proposed solution can be that the functionality of existing PPG based vital sign monitoring devices may be expanded at low cost. For example, a wrist-worn vital sign monitor may already comprise a PPG sensor and a communication interface. A wrist-worn monitoring device may be adapted to automatically raise an alert if a vital sign is not within a predetermined range, e.g. triggered by a vital sign indicative of the cardiovascular status. Having the possibility to manually trigger an alert may further improve the robustness of detect an event which needs medical attention.

A synergistic effect may be reached in that the PPG sensor may be used both for a vital-sign based medical alert as well as for a user-activated medical alert. A wrist-worn monitoring device may automatically raise an alert e.g. triggered by the cardiovascular status. Having the possibility to raise actively/manually an alert by moving the fingers, may increase the robustness to detect an event which needs medical attention. Hence, in addition or in the alternative to monitoring a cardiovascular state, it is suggested to use PPG for a user-activated alert system in case of emergency. The proposed solution of raising an alert may be lifesaving when other methods are not accessible, unavailable or out of reach.

According to an aspect of the present disclosure, a medical alarm or emergency message may thus be triggered by a recognized finger movement or gesture rather than a vital sign parameter. The first and second PPG signals may undergo pattern recognition as will be described further below.

In order to detect and identify finger movements in PPG signals, the technologies disclosed in WO2015/121100 A1 for the different application scenario of an input device for controlling a computer may advantageously be used. The disclosure of this earlier application of the same applicant is incorporated herein by reference in its entirety. In the present case, a much simpler PPG device may be used. In particular, in contrast to the aforementioned reference the PPG unit may not be adapted to generate light detection signals acquired at spatially different locations on the wrist (with different PPG sensors). In contrast to the device described in WO2015/121100 A1, the device according to the present disclosure may not be adapted to distinguish between different fingers. In the context of the present disclosure, light traveling through different regions of the tissue can be understood as using different wavelengths at the same location traveling through different layers of the tissue.

In an embodiment, the wrist-worn medical alert device can be adapted to establish an audio and/or video connection to a communication apparatus of the caregiver. Thereby, the caregiver may communicate with the subject to determine if and what kind of further assistance is required.

The processing unit can comprise a pattern recognition unit adapted to recognize a finger movement pattern of one or more fingers of the subject based on the first and second PPG signals. The communication unit can be adapted to transmit, based on the recognized finger movement pattern, an emergency message to the caregiver. For example, by moving one or more fingers in a certain rhythmic pattern, e.g. moving one finger up and down periodically, the PPG signals are disturbed and this disturbance can be extract as a pattern from the PPG signals. Depending on the recognized pattern, an alert may be raised. Examples of alert signals may be an alarm sound and/or a message delivered to the caregiver e.g. via the internet or a smart phone. A pattern may be determined by comparison with a predetermined waveform or spectrum.

The communication unit can be adapted to establish a connection to a first caregiver based on a first determined pattern; and to establish a connection to a second, different caregiver based on a second determined pattern. For example, if the subject does not require urgent assistance, he may choose a first finger movement pattern to establish a connection to a family member or neighbor. However, in an urgent medical case, he may choose a second finger movement pattern to establish a connection to a doctor. Hence, the pattern recognition unit may be adapted to recognize several different patterns.

In addition, or in the alternative, the communication unit can be adapted to transmit a first message based on a first determined pattern; and to transmit a second message based on a second determined pattern. In this way the user may convey different messages depending on the type of pattern generated with the finger movements. For example, different emergency messages or different severity levels may be indicated. Moreover, different messages may also be transmitted during communication with a caregiver. For example, the subject may not be able to speak but may transmit different messages such as yes/no or use messages such as Morse code for communication. For example, when an emergency message has been received by a caregiver a communication link may be established between the user and the caregiver, e.g. using audio/video. In case the user is not able to speak, the method can be used to communicate by replying to questions with fingers movements in patterns corresponding to 'yes' and 'no'.

In an embodiment, the processing unit can be adapted to determine (in particular based on the first and/or second PPG signal) a vital sign parameter of the subject and to adapt a threshold for determining the finger movement (or a threshold for pattern recognition) based on the determined vital sign parameter. An advantage of this embodiment is that an adaptive determination of finger movements or adaptive pattern recognition can be provided. For example, an emergency situation may correlate with arousal of the subject. Hence, there is a higher probability that the subject intends to issue emergency message if the subject the vital sign indicates a poor health state or if arousal of the subject is detected. A decision threshold may thus be lowered to more quickly respond to a finger movement in case of an emergency situation. An advantage can be that false alarms caused by finger movements can be reduced. This may complement the notion above to increase robustness by manually triggering an alert if the vital-sign based medical alert fails In an embodiment, the wrist-worn medical alert device can further comprise a motion sensor, such as e.g. an accelerometer or gyroscope, adapted to detect a motion of the subject, wherein the wrist-worn medical alert device is adapted not to generate an emergency message if the detected movement exceeds a predetermined threshold. An advantage of this embodiment is that false alarms can be suppressed. It is thus possible to further increase the accuracy. For example, only if no motion is determined or motion below threshold is determined by the accelerometer, an alert is issued. Moreover, the motion sensor may serve to avoid false alarms, i.e. to rule out motion components in the PPG signal stemming from movements other than finger movements.

In an embodiment, the wrist-worn medical alert device may further comprise a posture sensor adapted to determine a posture of the subject, wherein the wrist-worn medical alert device is adapted to adapt decision threshold for determining the finger movement and/or pattern recognition and/or to adapt a message content of the emergency message based on the determined posture. An advantage of this embodiment is that more meaningful alarms may be provided. For example, false alarms may be reduced since a standing subject is less likely to need medical assistance than a subject lying on the floor.

In an embodiment, the wrist-worn medical alert device can be operable in a learning mode, in which the device is adapted to learn patterns and corresponding emergency messages, and in a normal operation mode, in which the device is adapted to generate the emergency message corresponding to the learned patterns. An advantage of this embodiment is that the finger movement patterns can be adapted to the capabilities of the user. For example, a partially disabled subject may wish to perform different patterns than other subjects.

In an embodiment, the device wrist-worn medical alert device can be adapted to recognize at least one default pattern and to transmit a default emergency message to a communication apparatus of a caregiver upon determining the default pattern. An advantage of this embodiment is that the device can be shared or temporally assigned, e.g. to different patients during recovery.

In an embodiment, the processing unit can be adapted to monitor a ratio of the first and second PPG signals and to determine a finger movement of one or more fingers of the subject if the ratio changes by more than a predetermined threshold. For example, the processing unit may be adapted to analyze the amplitudes of red and green PPG signals acquired at red and green wavelengths to determine if an alert is to be issued.

In a further refinement, the first PPG signal is indicative of a measurement using red light and wherein the second PPG signal is indicative of a measurement using green light; and the processing unit can be adapted to determine a finger movement if an amplitude of the first (red) PPG signal is larger than an amplitude of the second (green) PPG signal. The red PPG signal has the property that during motion the signal amplitude is larger than the amplitude of the green signal, and when there is no motion, the amplitude of the red signal is smaller than the amplitude of the green signal (which may only contain the pulse component stemming from the heart contractions). Using this property of the signals, motion components triggered by finger movements can be detected.

Referring to the medical alert system, the base station can be configured to forward an emergency message from the wrist-worn medical alert device to a caregiver. An advantage of this embodiment is that the base station may serve as a relay. Thereby, the requirements and cost of the wrist-worn device in terms of one or more of cost, compatibility with transmission standards and power consumption may be reduced.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
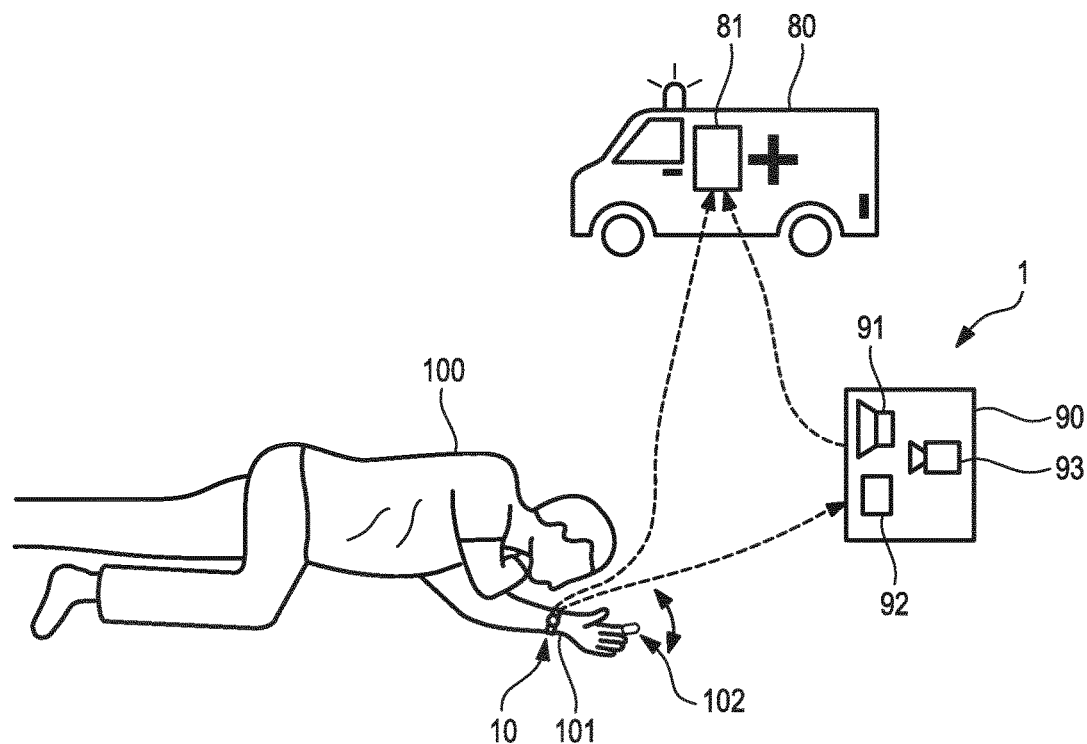
FIG. 1 shows an exemplary application scenario for a wrist-worn medical alert device for conveying an emergency message to a caregiver.

FIG. 1 shows an exemplary application scenario for using a wrist-worn medical alert device 10 for conveying an emergency message to a caregiver 80. A subject 100 may have experienced a medical emergency situation and is lying on the ground. The subject 100 may be partially immobilized, may not be able to get up by himself and may not even be able to reach for his phone to call for assistance.

On his wrist 101, the subject 100 wears a wrist-worn medical alert device 10, as will be described in more detail below. Even though the subject is not able to reach the wrist-worn medical alert device 10 with his other hand, the subject 100 can still transmit an emergency message to the caregiver 80. For example, the subject 100 may move his finger 102 up and down as indicated by the arrow in FIG. 1 or may tap on the floor. Based on the determined finger movement, the wrist-worn medical alert device 10 may then transmit an emergency message to the caregiver 80, more precisely to a communication apparatus 81 of the caregiver 80.

In the example shown in FIG. 1, the caregiver 80 is illustrated as an ambulance. However, the emergency message may also be transmitted to other types of caregivers such as family members, neighbors, a doctor or emergency service such as 911.

Optionally, the wrist-worn medical alert device 10 may form part of an alert system 1 for conveying an emergency message to a caregiver. The system may comprise the wrist-worn alert device 10 as well as a base station 90 configured to forward an emergency message from the wrist-worn medical alert device 10 to the caregiver 80. Hence, there is no need for the wrist-worn medical alert device to directly establish a connection to the caregiver in this embodiment. Instead, the base station 90 may act as a relay and forward the emergency message (an optionally add further message content such as address information) to the caregiver 80. Optionally, the base station may comprise a communication device for communicating with the subject 100, such as a speaker 91, a microphone 92 and/or a video camera 93. Thereby, the caregiver 80 may more easily communicate with the subject 100 in response to receiving the emergency message. It shall be understood that the communication device may also form part of the wrist-worn medical alert device 10.

In response to receiving the emergency message, the caregiver 80 may reach out to the subject 100. Known response protocols implemented for health buttons may be followed. For example, the caregiver 80 may try to contact the subject 100 via telephone in order to rule out a false alarm as a first step. If the subject 100 does not respond, assistance may be dispatched to the site of emergency.

Figure 2:
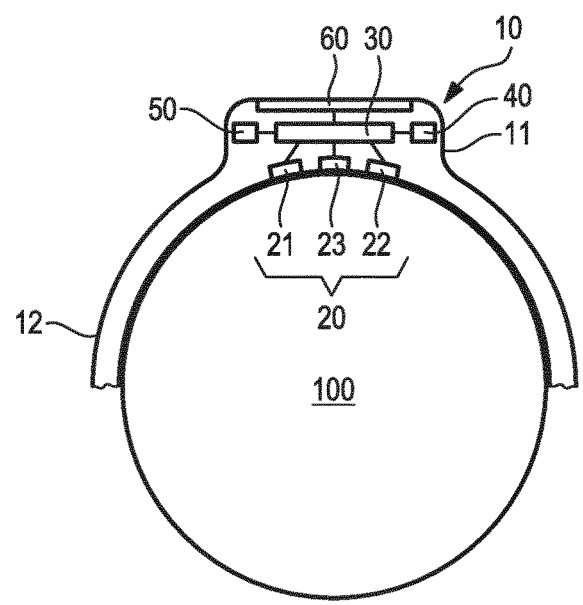
FIG. 2 shows an embodiment of a wrist-worn medical alert device.

FIG. 2 shows an exemplary embodiment of a wrist-worn medical alert device 10. In the present embodiment, the wrist-worn medical alert device 10 may be implemented in form of a (smart) watch comprising a housing 11 and a wristband 12.

The wrist-worn medical alert device 10 comprises a PPG unit 20, a processing unit 30 and a communication unit 40. Optionally a motion sensor 50 may be provided. Further, a human-machine interface 60 comprising a display, a microphone and/or a speaker may be provided as e.g. known in the field of wearable devices.

The PPG unit 20 is adapted to acquire a first PPG signal at first wavelength ($\lambda 1$) and a second PPG signal at second wavelength ($\lambda 2$) over time at the wrist of the subject.

Photoplethysmography (PPG) is a known technology that can be used to monitor perfusion. PPG is an optical measurement technique that evaluates a time-variant change of light reflectance or transmission of an area or volume of interest. PPG is based on the principle that blood absorbs light (more than surrounding tissue), so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared or red and green), the blood oxygen saturation can be determined.

The acquired waveforms are susceptible to motion of the PPG unit relative to the measured tissue as well as to changes within the tissue, e.g. due to a muscular activity or movement of tendons. Hence, even though a wrist-worn PPG unit 20 does not directly observe the fingers 102 of the subject 100 (see FIG. 1), the "actuators" for causing a finger movement can be effectively monitored using PPG. Any movement of said actuators or structures affected by said movement may translate to a contribution to the PPG signals. However, instead of disregarding these contributions as artifacts, it is suggested to determine a finger movement based on the effect of said actuators on the PPG signals.

PPG units are known in the art. Photoplethysmography has been widely used over the past for the estimation of cardiovascular parameters. The PPG unit 20 can comprise a first light source 21 adapted to emit light at a first wavelength towards a tissue region of the wrist of the subject; a second light source 22 adapted to emit light at a second wavelength towards the tissue region of the subject, and a photodetector 23 adapted to detect light received from the tissue region of the subject. The PPG unit 20 can be adapted to acquire a first PPG signal over time by detecting radiation received from said tissue region in response to light the first wavelength being emitting towards the tissue region of the subject; and to acquire a second PPG signal over time by detecting radiation received from said tissue region in response to light at the second wavelength being emitted towards the tissue region of the subject. The first PPG signal is thus indicative of an absorption of light at a first wavelength ($\lambda 1$) over time having travelled through a tissue region of the wrist of the subject, and the second PPG signal is indicative of an absorption of light at a second wavelength ($\lambda 2$) over time having travelled through the tissue region of the wrist of the subject. A tissue region in this context may refer to a probed wrist location. Light at the first and at the second wavelength may probe the tissue region at different depths (instead of at different wrist locations).

The processing unit 30 is adapted to receive the first and second PPG signals and to determine a finger movement of one or more fingers of the subject based on the first and second PPG signals. For example, the processing unit may be adapted to analyze the first and second PPG signals for patterns indicative of a finger movement. In particular, the processing unit may comprise a pattern recognition unit adapted to recognize a finger movement pattern of one or more fingers of the subject based on the first and second PPG signals; and wherein the communication unit is adapted to transmit, based on the recognized finger movement pattern, an emergency message to the caregiver. Based on the determined finger movement, the communication unit 40 is adapted to transmit an emergency message to the caregiver 80 (see FIG. 1). Further details of an exemplary embodiment will be described with reference to the block diagram of FIG. 3.

Optionally, an acknowledgement may be provided from the caregiver 80 to the subject 100. The wrist-worn medical alert device may be adapted to signal the acknowledgement to the subject 100. For example, the acknowledge may be signaled to the subject 100 as a visual and/or audible signal. In addition, or in the alternative, the acknowledge may be signaled as a tactile stimulus, such as a vibration at a wrist of the subject. An advantage of this embodiment is that the subject may receive feedback that his emergency message is taken care of even if the subject may not see or hear a visual or audible acknowledgement.

The HMI 60 may be used for interaction with the caregiver in response to transmitting the emergency message to the caregiver. In an advantageous embodiment, an audio and/or video connection may be established to a communication apparatus of the caregiver so that the caregiver can immediately check on the subject.

Figure 3:
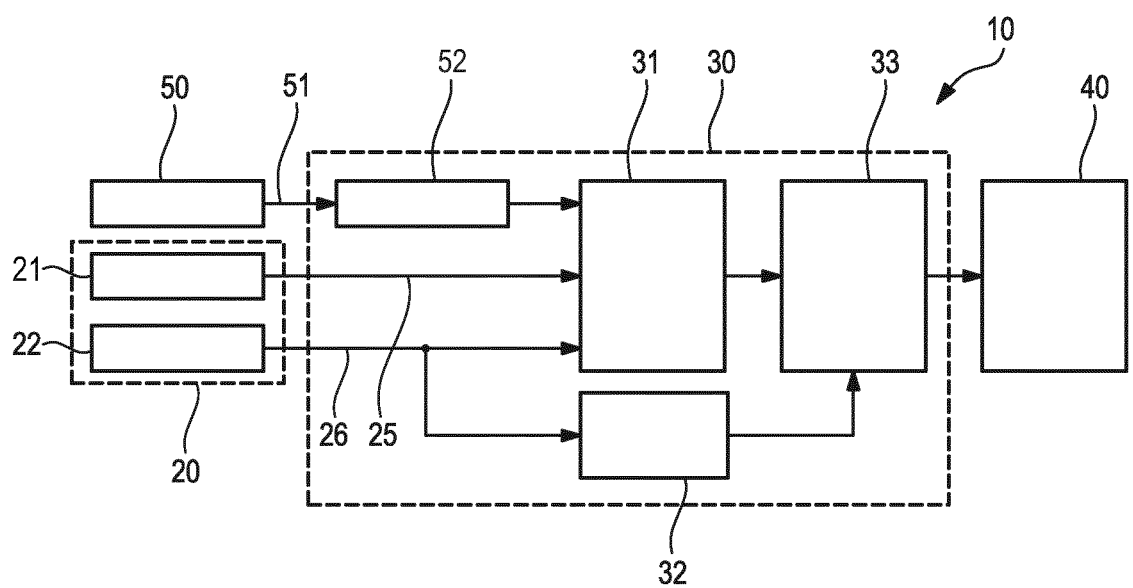
FIG. 3 shows a block diagram of an embodiment of a wrist-worn medical alert device.

FIG. 3 shows a block diagram of a wrist-worn medical alert device base on multi-color PPG according to an exemplary embodiment. The PPG unit 20 is configured to provide a first PPG signal 26 indicative of a measurement using red light and a second PPG signal 25 is indicative of a measurement using green light. The PPG unit may be configured as shown in FIG. 2 comprising a red light source 22 and a green light source 21 for measurement of the respective PPG signals 25, 26. A common photodetector 23 may be used or a separate photodetector may be used for or co-integrated with the respective light sources 21, 22. The PPG signals 25, 26 are provided to the processing unit 30.

In an embodiment, the processing unit 30 may comprise a finger movement detection unit 31 adapted to detect a movement of one or more fingers.

Optionally, a motion detector 50 such as an accelerometer or gyroscope may be provided. For example, the accelerometer may provide an acceleration signal 51. The acceleration signal may be provided to a motion detection unit 52 adapted to determine a motion above a predetermined threshold. The motion detection unit may be part of the motion detector 50 or part of the signal processing unit 30 or provided as a separate signal processing device. A motion detection unit 52 may be introduced to avoid false alarms from motion components of other sources, i.e., non-finger movements such as walking or just moving the arm. The accelerometer hardly detects motion of the fingers, whereas the red and green PPG detect movements from the fingers very well. To exclude motions stemming from other sources than the fingers, the processing unit can be adapted to discard the finger movement detection when a motion level (such as an L1 or L2 norm of tri-axial accelerometer signals) computed from the accelerometer signal exceeds a predetermined threshold.

Figure 4:
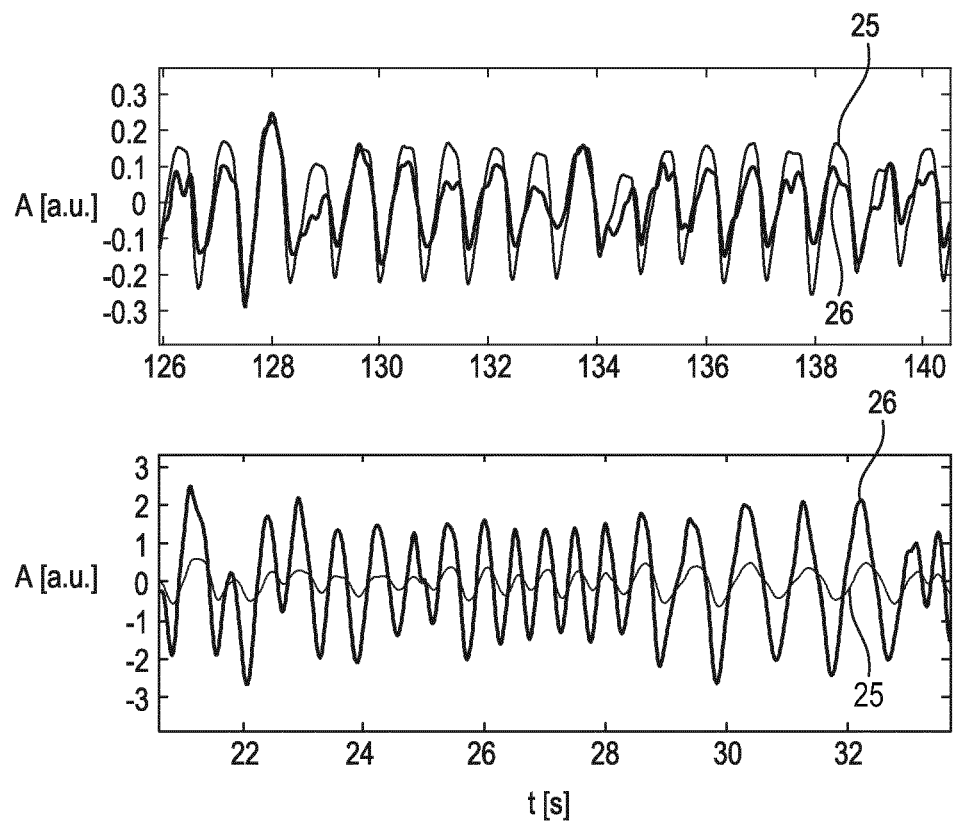
FIG. 4 shows diagrams of exemplary PPG signals.

FIG. 4 shows diagrams of exemplary green 25 and red 26 PPG waveforms recorded with a wrist-worn multi-color PPG-based medical alert device 10 according to an aspect of the present disclosure. The upper graph in FIG. 4 shows a recording in rest when no fingers are moved and the motion level computed by the accelerometer signals is below a predetermined threshold. The signals contain the pulse component which stems from the contraction of the heart. The lower graph in FIG. 4 shows the green 25 and red 26 PPG signals when the fingers are moved periodically. In both cases, no motion is detected by the accelerometer. The periodicity seen in both signals in the lower graph comes from the periodic motion generated by the fingers, masking the much smaller pulse component.

What can be clearly observed in the upper graph in FIG. 4 is that for the motionless recording the variation of the red PPG signal 26 is smaller than the variation of the green PPG signal 25. The variation of the red PPG signal 26 in the bottom graph, however, is clearly larger than the variation of the green PPG signal 25 during finger movements. The inventor has found that this property can be used to determine whether the signals are stemming from heart contractions or stemming from finger movements.

Hence, the processing unit 30 can be adapted to monitor a ratio of the first and second PPG signals 25, 26 and to determine a finger movement of one or more fingers of the subject if the ratio changes by more than a predetermined threshold. In particular, the first PPG signal can be indicative of a measurement using red light 26 and the second PPG signal 25 can be indicative of a measurement using green light. The processing unit can be adapted to determine a finger movement if an amplitude of the first PPG signal 26 is larger than an amplitude of the second PPG signal 25 and/or if a ratio of the first PPG signal 26 with respect to the second PPG signal 25 changes. An advantage of this embodiment is that a non-computationally intensive approach is presented to determine a finger movement.

Referring again to the embodiment of FIG. 3, the processing unit 30, in particular the finger movement detection unit 31 can be adapted to detect a finger movement based on the first and second PPG signals and optionally based on the motion of the subject as provided by the motion sensor 50. In an embodiment, a finger movement can be detected when (1) the motion level based on the motion sensor signals, such as accelerometer signals is below a predetermined threshold, and (2) the variation of the red PPG signal 26 is larger than the variation of the green PPG signal 25. Step (1) in this embodiment may be optional. An example to measure the variation is by taking the root mean square (RMS) at sample n of the signals, i.e.

$$RMS_g(n) = \sqrt{\frac{1}{L}\sum_{i=n-L+1}^{n}(C_1 \cdot g(i))^2},$$

$$RMS_r(n) = \sqrt{\frac{1}{L}\sum_{i=n-L+1}^{n}(C_2 \cdot r(i))^2},$$

where g(i) and red r(i) are samples of the green and red PPG signal, $C_1$ and $C_2$ can be optional scalars to compensate for calibration, e.g. depending on the type of sensor and LED power, L the length of the sliding window and n, i the sample index. If e.g. the ratio $$\frac{RMS_r(n)}{RMS_g(n)} < K$$

for a predetermined threshold K, the detection may be discarded.

The processing unit 30 can, in addition or in the alternative, comprise a pattern recognition unit adapted to recognize a finger movement pattern of one or more fingers of the subject based on the first and/or second PPG signals 25, 26. The communication unit can be adapted to transmit, based on the recognized finger movement pattern, an emergency message to the caregiver. Referring to FIG. 4, the processing unit 30 may comprise a pattern recognition unit 32 adapted to determine whether a correct pattern is used for generating an alert. Optionally, the pattern to be evaluated can be decided or trained by the user.

Figure 5:
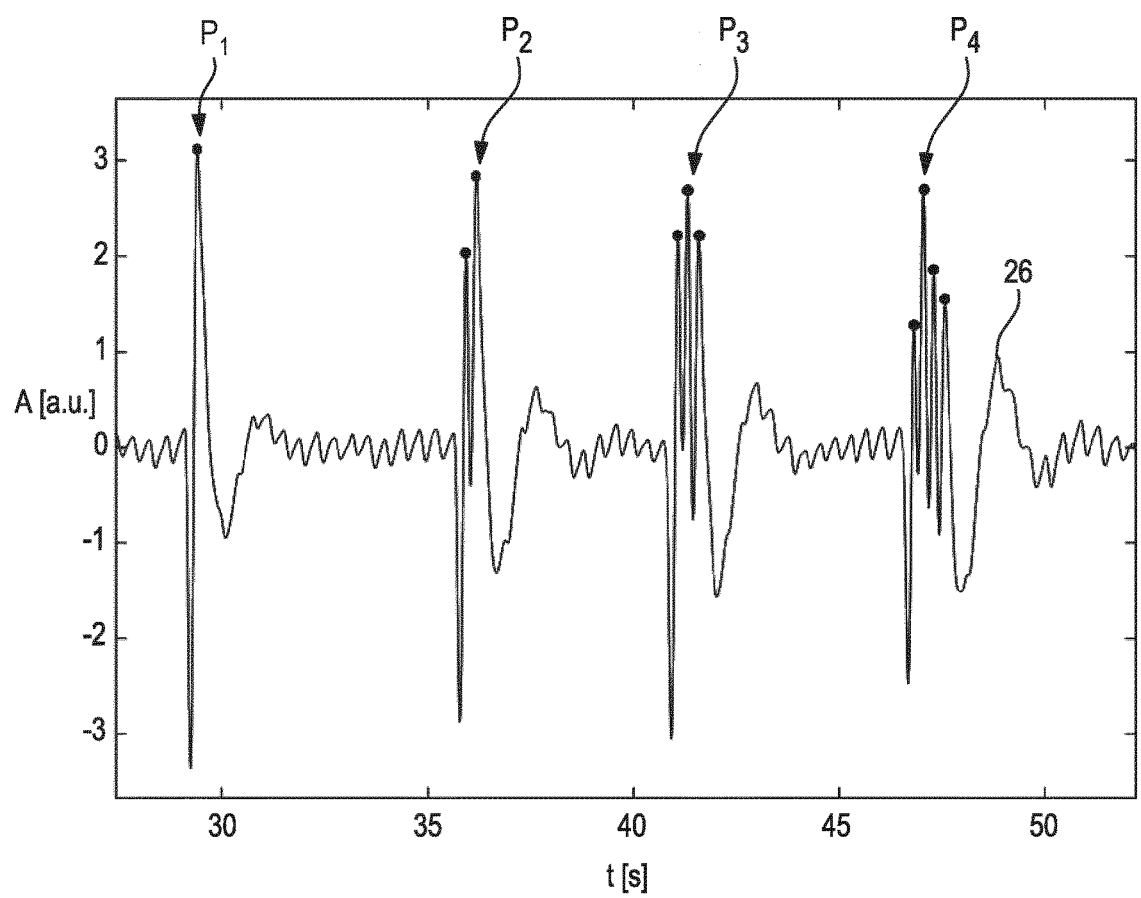
FIG. 5 shows a further diagram of an exemplary signal.

FIG. 5 shows an example of a set of four patterns P1, P2, P3, and P4 indicative of 1, 2, 3 and 4 consecutive taps generated by the index finger, as indicated by the black dots.

In an embodiment, both the output of the finger movement detection unit 31 and the output of the pattern recognition unit 32 may be used to determine whether an emergency message should be transmitted to the caregiver. A decision unit 33 may thus be adapted to receive the output of the finger movement detection unit 31 and the pattern recognition unit 32 and to determine whether the emergency message should be issued. The emergency message may then be transmitted to a caregiver via the communication unit 40. Alternatively, only the detection unit 31 or the pattern recognition unit may be evaluated.

In an advantageous refinement, the pattern recognition unit 32 may be adapted to determine at least a first and a second pattern and the communication unit 40 can be adapted to establish a connection to a first caregiver based on a first determined pattern; and to establish a connection to a second, different caregiver based on a second determined pattern. In addition, or in the alternative, the communication unit 40 can be adapted to transmit a first message based on a first determined pattern; and to transmit a second message based on a second determined pattern (e.g. patterns P2 and P4, as shown in FIG. 5). In other words, the pattern recognition unit 32 may be adapted to recognize several different patterns. In this way the user may convey different messages depending on the type of pattern generated with the finger movements.

In addition, or in the alternative, when an emergency message has been received by a caregiver a communication link may be established between the user and the caregiver, e.g. using audio and/or video. For example, in case the user is not able to speak, the solution proposed herein can further be used to communicate with the caregiver, e.g. by replying to questions with fingers movements in patterns corresponding to answers such as 'yes' and 'no'.

Figure 6:
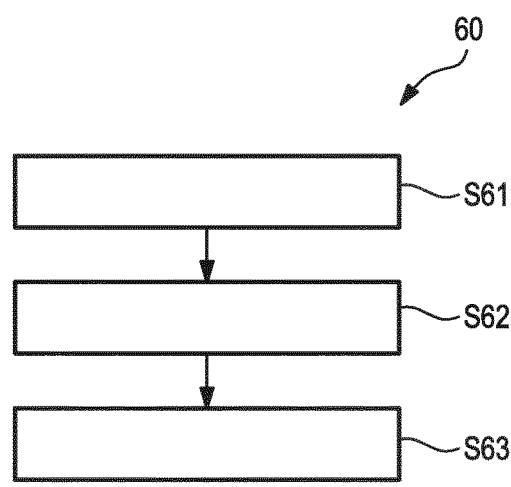
FIG. 6 shows a block diagram of a medical alert method for conveying an emergency message to a caregiver.

FIG. 6 shows a flowchart of a medical alert method 60 for conveying an emergency message to a caregiver. In a first step S61, a first PPG signal and a second PPG signal are received, said first PPG signal being acquired at a first wavelength (λ1) and said second PPG signal being acquired at a second wavelength (λ2) over time at a wrist of a subject. In a second step S62, a finger movement of one or more fingers of the subject is determined based on the first and second PPG signals. In a third step S63, an emergency message is transmitted to the caregiver based on the determined finger movement.

In conclusion an advantageous medical alert device, system and method are presented that may more easily be operated by a user. In particular, the solutions described herein may facilitate the dispatch of an alert or emergency message in a wider range of emergency situations.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. Wrist-worn medical alert device for conveying an emergency message to a caregiver, the device comprising:
    a photoplethysmography (PPG) unit adapted to acquire a first PPG signal at a first wavelength and a second PPG signal at a second wavelength over a first time period at a wrist of a subject;
    a processing unit adapted to receive the first and second PPG signals and to determine a finger movement of one or more fingers of the subject based on the first and second PPG signals, wherein finger movement is determined if a ratio of the first PPG signal and the second PPG signal changes during the first time period by more than a predetermined threshold; and
    a communication unit adapted to transmit, based on the determined finger movement, an emergency message to the caregiver.

2. Wrist-worn medical alert device according to claim 1, adapted to establish an audio and/or video connection to a communication apparatus of the caregiver.

3. Wrist-worn medical alert device according to claim 1, wherein the processing unit comprises a pattern recognition unit adapted to recognize a finger movement pattern of one or more fingers of the subject based on the first and/or second PPG signals; and wherein the communication unit is adapted to transmit, based on the recognized finger movement pattern, an emergency message to the caregiver.

4. Wrist-worn medical alert device according to claim 3, wherein the communication unit is adapted to establish a connection to a first caregiver based on a first determined pattern; and to establish a connection to a second, different caregiver based on a second determined pattern.

5. Wrist-worn medical alert device according to claim 3, wherein the communication unit is adapted to transmit a first message based on a first determined pattern; and to transmit a second message based on a second determined pattern.

6. Wrist-worn medical alert device according to claim 1, wherein the processing unit is adapted to determine, in particular based on the first and/or second PPG signal, a vital sign parameter of the subject and to adapt a threshold for determining the finger movement based on the determined vital sign parameter.

7. Wrist-worn medical alert device according to claim 1, further comprising a motion sensor adapted to detect a motion of the subject, wherein the wrist-worn medical alert device is adapted not to generate an emergency message if the detected movement exceeds a predetermined threshold.

8. Wrist-worn medical alert device according to claim 1, further comprising a posture sensor adapted to determine a posture of the subject, wherein the wrist-worn medical alert device is adapted to adapt decision threshold for determining the finger movement and/or to adapt a message content of the emergency message based on the determined posture.

9. Wrist-worn medical alert device according to claim 1, wherein the device is operable in a learning mode, in which the device is adapted to learn patterns and corresponding emergency message(s), and in a normal operation mode, in which the device is adapted to generate the emergency message corresponding to the learned pattern.

10. Wrist-worn medical alert device according to claim 1, wherein the device is adapted to recognize at least one default pattern and to transmit a default emergency message to a communication apparatus of a caregiver upon determining the default pattern.

11. Wrist-worn medical alert device according to claim 1, wherein the first PPG signal is indicative of a measurement using red light and wherein the second PPG signal is indicative of a measurement using green light; and
wherein the processing unit is adapted to determine a finger movement if an amplitude of the first PPG signal is larger than an amplitude of the second PPG signal.

12. Medical alert system for conveying an emergency message to a caregiver, the system comprising:
the wrist-worn medical alert device according to claim 1; and
a base station configured to forward an emergency message from the wrist-worn medical alert device to the caregiver.

13. Medical alert method for conveying an emergency message to a caregiver, the method comprising the steps of:
receiving first and second photoplethysmography (PPG) signals, said first PPG signal being acquired at a first wavelength and said second PPG signal being acquired at a second wavelength over time at a wrist of a subject;
determining a finger movement of one or more fingers of the subject based on the first and second PPG signals, wherein finger movement is determined if a ratio of the first PPG signal and the second PPG signal changes during the first time period by more than a predetermined threshold; and
transmitting, based on the determined finger movement, an emergency message to the caregiver.

14. A non-transitory computer-readable medium comprising program code means for causing a computer to carry out the steps of the method as claimed in claim 13.

15. The method of claim 13, wherein the first PPG signal is indicative of a measurement using red light and wherein the second PPG signal is indicative of a measurement using green light; and
wherein the processing unit is adapted to determine a finger movement if an amplitude of the first PPG signal is larger than an amplitude of the second PPG signal.

* * * * *